US010562866B2

(12) United States Patent
Prasad et al.

(10) Patent No.: US 10,562,866 B2
(45) Date of Patent: Feb. 18, 2020

(54) AMORPHOUS TRISODIUM SACUBITRIL VALSARTAN AND A PROCESS FOR THE PREPARATION THEREOF

(71) Applicant: Mylan Laboratories Ltd., Hyderabad (IN)

(72) Inventors: Vellanki Sivaram Prasad, Telangana (IN); Arabinda Sahu, Telangana (IN); Siva Koteswara Rao Prathi, Telangana (IN); Lakshmana Rao Ampolu, Telangana (IN); Ramakoteswara Rao Jetti, Telangana (IN); Aggi Ramireddy Bommareddy, Telangana (IN); Neelima Bhagavatula, Telangana (IN); Nitin Ashok Shimpi, Telangana (IN)

(73) Assignee: Mylan Laboratories Limited, Hyderabad (IN)

( * ) Notice: Subject to any disclaimer, the term of this patent is extended or adjusted under 35 U.S.C. 154(b) by 14 days.

(21) Appl. No.: 15/568,550

(22) PCT Filed: Feb. 6, 2016

(86) PCT No.: PCT/IB2016/050622
§ 371 (c)(1),
(2) Date: Oct. 23, 2017

(87) PCT Pub. No.: WO2016/125123
PCT Pub. Date: Aug. 11, 2016

(65) Prior Publication Data
US 2018/0273493 A1  Sep. 27, 2018

(30) Foreign Application Priority Data

Feb. 6, 2015  (IN) .............................. 602/CHE/2015
Jul. 10, 2015  (IN) ........................... 3531/CHE/2015

(51) Int. Cl.
*C07D 257/04* (2006.01)
*C07C 231/12* (2006.01)
*C07C 231/24* (2006.01)

(52) U.S. Cl.
CPC .......... *C07D 257/04* (2013.01); *C07C 231/12* (2013.01); *C07C 231/24* (2013.01); *C07B 2200/13* (2013.01)

(58) Field of Classification Search
CPC ........................... C07C 235/82; C07D 257/04
See application file for complete search history.

(56) References Cited

U.S. PATENT DOCUMENTS

| 8,877,938 | B2 * | 11/2014 | Feng | .................... | A61K 31/216 |
| | | | | | 548/253 |
| 2004/0072886 | A1 * | 4/2004 | Reguri | ................. | C07D 257/04 |
| | | | | | 514/381 |
| 2009/0156585 | A1 * | 6/2009 | Feng | .................... | A61K 31/216 |
| | | | | | 514/223.5 |
| 2016/0206597 | A1 * | 7/2016 | Bransford | ............ | A61K 31/194 |
| 2016/0213646 | A1 * | 7/2016 | Shi | ......................... | A61K 45/06 |

FOREIGN PATENT DOCUMENTS

| CN | 105461647 | A | * | 4/2016 | | |
| EP | 1950204 | A1 | * | 7/2008 | ......... | C07D 257/04 |
| EP | 3117823 | A1 | * | 1/2017 | .............. | A61K 9/19 |
| WO | WO2007056546 | A1 | | 5/2007 | | |
| WO | WO-2010091169 | A2 | * | 8/2010 | ......... | C07D 257/04 |
| WO | WO-2016125123 | A1 | * | 8/2016 | ............ | A61K 31/41 |
| WO | WO-2017009784 | A1 | * | 1/2017 | ......... | C07D 257/04 |
| WO | WO-2017012917 | A1 | * | 1/2017 | ................ | A61P 9/12 |
| WO | WO-2017037591 | A1 | * | 3/2017 | ............ | A61K 31/41 |

OTHER PUBLICATIONS

Craig International Journal of Pharmaceuticals 179 (1999) 179-207. (Year: 1999).*
MA International Journal of Pharmaceutics 441 (2013) 75-81 (Year: 2013).*
Lili Feng et al: "LCZ696: a dual-acting sodium supramolecular complex", Tetrahedron Letters, Pergamon, GB, vol. 53, No. 3, Nov. 5, 2011 (Nov. 5, 2011), pp. 275-276, XP028393477, ISSN: 0040-4039, retrieved on Nov. 15, 2011], DOI: 10.1016/J.TETLET.2011.11.029.

* cited by examiner

*Primary Examiner* — Matthew P Coughlin

(57) ABSTRACT

The amorphous form of trisodium sacubitril valsartan and methods for the preparation thereof are disclosed herein.

15 Claims, 1 Drawing Sheet

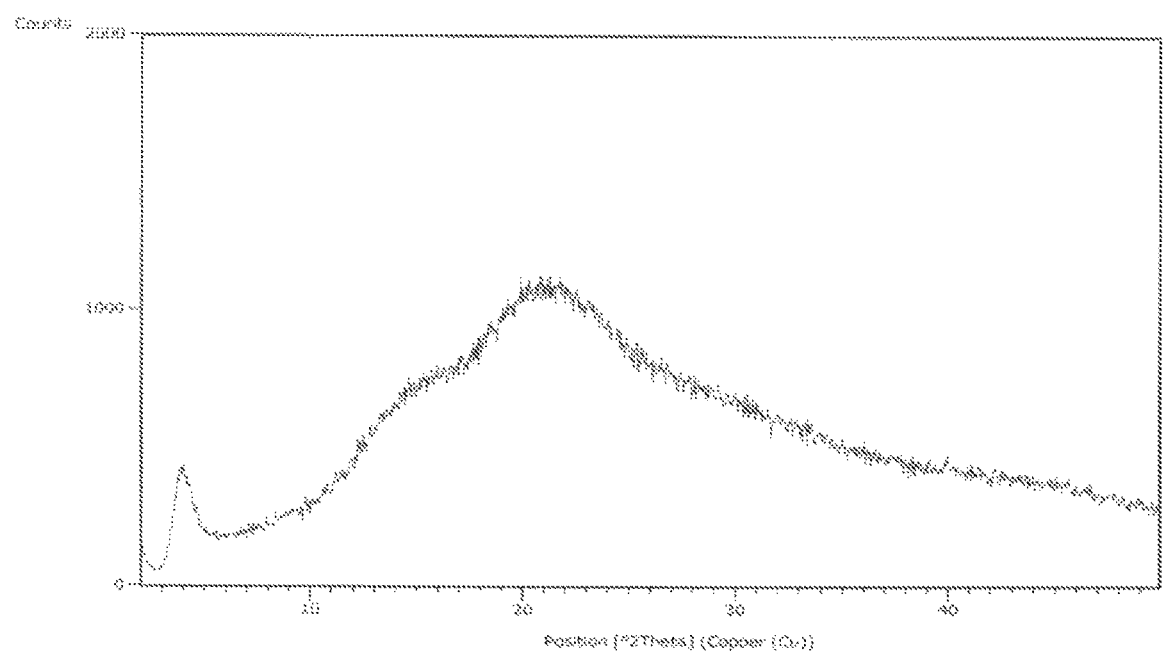
Figure 1 shows a powder X-ray diffraction pattern of the amorphous Trisodium Sacubitril Valsartan complex.

AMORPHOUS TRISODIUM SACUBITRIL VALSARTAN AND A PROCESS FOR THE PREPARATION THEREOF

CROSS-REFERENCE TO RELATED APPLICATIONS

This application claims the benefit of Indian provisional patent application nos. 602/CHE/2015 filed on Feb. 6, 2015 and 3531/CHE/2015 filed on Jul. 10, 2015, which are hereby incorporated by reference in their entirety.

BACKGROUND OF THE INVENTION

Field of the Invention

The present invention relates generally to active pharmaceutical agents and method for their preparation and more specifically to an amorphous form of trisodium sacubitril valsartan and processes for the preparation thereof.

Background of the Invention

Sacubitril valsartan, also known as LCZ696, is a co-crystallized complex of valsartan and sacubitril in a 1:1 molar ratio. Chemically, valsartan is known as (S)-3-methyl-2-(N-{[2'-(2H-1,2,3,4-tetrazol-5-yl)biphenyl-4-yl]methyl}pentanamido)butanoic acid and sacubitril is known as 4-{[(2S,4R)-1-(4-biphenylyl)-5-ethoxy-4-methyl-5-oxo-2-pentanyl]amino}-4-oxobutanoic acid. LCZ696 consists of 6 valsartan anions, 6 sacubitril cations, 18 sodium cations, and 15 molecules of water. Sacubitril valsartan is marketed under the trade name ENTRESTO® by Novartis. The reduced formula of the sacubitril valsartan, as included in the ENTRESTRO® product, is shown below as Formula-I as a single valsartan molecule with a single sacubitril molecule together with three sodium anions and 2.5 water molecules.

Sacubitril is a neprilysin inhibitor and valsartan is an angiotensin II receptor blocker. ENTRESTO® is indicated to reduce the risk of cardiovascular death and hospitalization for heart failure in patients with chronic heart failure (NYHA Class II-IV) and reduced ejection fraction.

U.S. Pat. No. 8,877,938 discloses a supramolecular complex of trisodium sacubitril valsartan hemipentahydrate in crystalline form.

The present invention provides amorphous trisodium sacubitril valsartan as well as a process for the preparation thereof. Amorphous trisodium sacubitril valsartan may provide different advantages in a variety of capacities, for example, in formulation, stability of the form, stability of the formulation, and in pharmacokinetic profiles. Within the context of the present disclosure, Trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] will be referred to as "trisodium sacubitril valsartan."

SUMMARY OF THE INVENTION

The present invention provides amorphous trisodium sacubitril valsartan as well as processes for the preparation thereof.

Another aspect of the present invention provides a process for the preparation of amorphous trisodium sacubitril valsartan, which may include the following steps:

a) dissolving trisodium sacubitril valsartan in a solvent; and b) removing the solvent to isolate amorphous trisodium sacubitril valsartan.

Another aspect of the present invention provide process for the preparation of amorphous trisodium sacubitril valsartan, which may include the following steps:

a) dissolving trisodium sacubitril valsartan in a first solvent to form a solution;

b) adding second solvent to the solution; and c) isolating amorphous trisodium sacubitril valsartan.

Another aspect of the present invention provides a process for the preparation of amorphous trisodium sacubitril valsartan, which may include the following steps:

a) dissolving valsartan and sacubitril in a solvent to form a solution;

b) adding sodium source to the solution; and c) removing the solvent to isolate amorphous trisodium sacubitril valsartan.

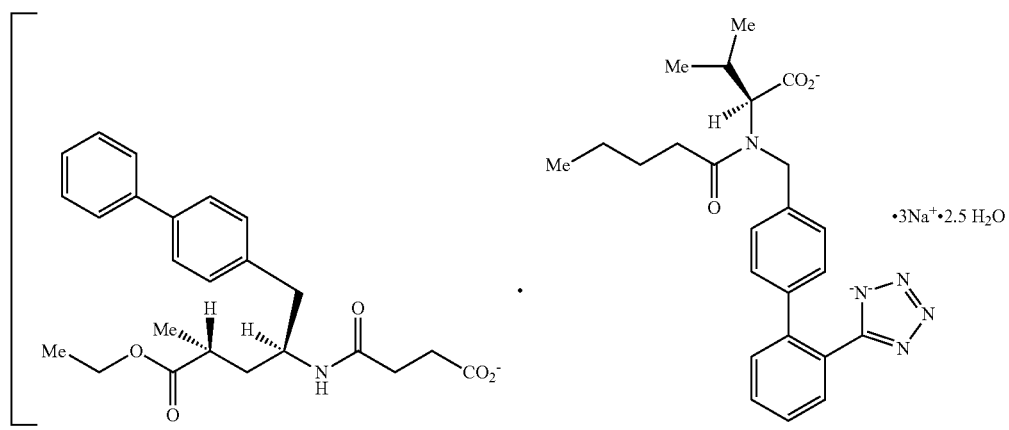

Formula-I

A further aspect of the present invention provides a process for the preparation of amorphous trisodium sacubitril valsartan, which may include the following steps:

a) dissolving sacubitril and valsartan in a first solvent to form a first solution;

b) adding a sodium source the first solution;

c) removing the first solvent to form a reaction mass;

d) adding a second solvent to the reaction mass to form a second solution;

e) adding a third solvent to second solution; and f) isolating amorphous trisodium sacubitril valsartan.

A further aspect of the present invention provides a process for the preparation of amorphous trisodium sacubitril valsartan, which may include the following steps:

a) dissolving trisodium sacubitril valsartan in a polar solvent to form a solution;
b) adding the solution to a non-polar solvent, and
c) isolating amorphous trisodium sacubitril valsartan.

The amorphous form of trisodium sacubitril valsartan of the present invention may be used in the formulation of oral pharmaceutical dosage forms. These oral pharmaceutical dosage forms may include pharmaceutically acceptable excipients in addition to trisodium sacubitril valsartan.

BRIEF DESCRIPTION OF THE DRAWINGS

Further aspects of the present disclosure together with additional features contributing thereto and advantages accruing there from will be apparent from the following description of embodiments of the disclosure which are shown in the accompanying drawing wherein:

FIG. 1 is a powder X-ray diffraction pattern of amorphous trisodium sacubitril valsartan.

DETAILED DESCRIPTION OF THE INVENTION

It is to be understood that the figures and descriptions of the present invention have been simplified to illustrate elements that are relevant for a clear understanding of the invention. The detailed description will be provided herein below with reference to the attached drawing.

The present invention provides an amorphous form of trisodium sacubitril valsartan and processes for the preparation thereof.

One aspect of the present invention provides an amorphous form of trisodium sacubitril valsartan. According to the present invention, the amorphous form of trisodium sacubitril valsartan may be characterized as amorphous by the powder X-ray diffraction (PXRD) pattern in FIG. 1.

The amorphous form of the trisodium sacubitril valsartan disclosed herein may be characterized as such by its X-ray powder diffraction (PXRD) pattern. Thus, the PXRD pattern of amorphous trisodium sacubitril valsartan was measured on a Panalytical X'pert Pro powder X-ray diffractometer equipped with goniometer of θ/2θ configuration and X'celerator detector. The Cu-anode X-ray tube was operated at 40 kV and 30 mA. The experiments were conducted over the 2θ range of 2.0°-50.0°, 0.030° step size and 50 seconds step time.

Within the context of the present invention, the amorphous form of trisodium sacubitril valsartan is not crystalline, but rather is an amorphous solid of trisodium sacubitril valsartan, wherein the molar ratio of sacubitril to valsartan is, on average, 1:1. In some embodiments of the present invention, the trisodium sacubitril valsartan may contain up to 8% water. In some embodiments, the moisture content may be less than 8%, less than 6%, less than 4%, less than 2%, less than 1%, or less than 0.1%.

Another aspect of the present invention provides a process for the preparation of amorphous trisodium sacubitril valsartan, which may include the following steps:

a) dissolving trisodium sacubitril valsartan in a solvent; and
b) removing the solvent to isolate amorphous trisodium sacubitril valsartan.

This embodiment of the present invention may be practiced by first dissolving trisodium sacubitril valsartan (in any crystalline or solvated form) in a solvent. Examples of suitable solvents include alcohol solvents, ketone solvents, ester solvents, ether solvents, water, or mixtures thereof. Examples of suitable alcohol solvents include methanol, ethanol, propanol, isopropanol, and mixtures thereof. Examples of suitable ketone solvents include acetone, methyl ethyl ketone, methyl isobutyl ketone, and mixtures thereof. Examples of suitable ester solvents may be methyl acetate, ethyl acetate, isopropyl acetate, tert-butyl acetate, or mixtures thereof. Examples of suitable ether solvents include tetrahydrofuran, diethyl ether, 1,4-dioxane, methyl tert-butyl ether, and mixtures thereof. In certain embodiments of the present invention, water or methanol was found to be a particularly useful solvent.

Next, the solvent may be removed to isolate amorphous trisodium sacubitril valsartan. This may be achieved by methods well known in the art, for example, by evaporation, distillation, spray drying, lyophilization, or agitated thin film drying.

Another aspect of the present invention encompasses additional processes for the preparation of amorphous trisodium sacubitril valsartan, which may include the following steps:

a) dissolving trisodium sacubitril valsartan in a first solvent to form a solution;
b) adding a second solvent to the solution; and
c) isolating amorphous trisodium sacubitril valsartan.

This embodiment of the present invention may be practiced by first dissolving trisodium sacubitril valsartan in a first solvent. Within the context of the present invention, the trisodium sacubitril valsartan may be any crystalline or solvated form. Examples of suitable solvents for use in this step include polar solvents such as alcohol solvents, ester solvents, and ketone solvents. Examples of suitable alcohol solvents include methanol, ethanol, isopropanol, and mixtures thereof. Examples of suitable ester solvents include methyl acetate, ethyl acetate, isopropyl acetate, tert-butyl acetate, and mixtures thereof. Examples of suitable ketone solvents include acetone, methyl ethyl ketone, methyl isobutyl ketone, and mixtures thereof. In some embodiments of the present invention, using tert-butyl acetate as the first solvent was found to be particularly useful.

Dissolving trisodium sacubitril valsartan may be achieved at an elevated temperature, for example, about 90° C. to about 110° C.

In some embodiments of the invention, the solution may be cooled, for example, to a temperature of about 20° C. to about 50° C.

Next, a second solvent may be added to the solution. The second solvent may be, for example, a non-polar solvent such as an ether solvent or a hydrocarbon solvent. Suitable ether solvent include, for example, diethyl ether, diisopropyl ether, methyl tert-butyl ether, and mixtures thereof. Suitable hydrocarbon solvents include $C_5$-$C_7$ straight-chain alkanes or $C_5$-$C_7$ cycloalkanes, for example, pentane, hexane, heptane, cyclohexane, and mixtures thereof. Within the context of this embodiment, addition of the second solvent may cause a solid to precipitate out of solution.

Amorphous trisodium sacubitril valsartan may then be isolated. Isolation may be carried out by methods well known in the art, for example, by filtering and drying the obtained solid.

Another aspect of the present invention provides a process for the preparation of amorphous trisodium sacubitril valsartan, which may include the following steps:

a) dissolving valsartan and sacubitril in a solvent to form a solution;

b) adding sodium source to the solution; and c) removing the solvent to isolate amorphous trisodium sacubitril valsartan.

This embodiment of the present invention may be practiced by first dissolving valsartan and sacubitril in a solvent. The solvent may be an alcohol solvent, an ether solvent, an ester solvent, a ketone solvent, an amide solvent, dimethyl sulfoxide, or mixtures thereof.

Examples of suitable alcohol solvents include methanol, ethanol, isopropanol, and mixtures thereof. Example of suitable ether solvents include tetrahydrofuran, diethyl ether, 1,4-dioxane, methyl tert-butyl ether, and mixtures thereof. Examples of suitable ester solvents include methyl acetate, ethyl acetate, isopropyl acetate, tert-butyl acetate, and mixtures thereof. Examples of suitable ketone solvents include acetone, methyl ethyl ketone, methyl isobutyl ketone, and mixtures thereof. Examples of suitable amide solvents include dimethylacetamide, dimethylformamide, and mixtures thereof. In particularly useful embodiments, tetrahydrofuran is used as a solvent in this step.

A sodium source may then be added to the solution. Examples of suitable sodium sources include sodium hydroxide, sodium alkoxide, and sodium 2-ethylhexonate. In particularly useful embodiments, sodium hydroxide or sodium methoxide is used as a sodium source.

Next, the solvent may be removed to isolate amorphous trisodium sacubitril valsartan. This may be carried out by techniques well-known in the art, for example, evaporation, distillation, spray drying, or agitated thin film drying.

A further aspect of the present invention provides an additional process for the preparation of amorphous trisodium sacubitril valsartan, which may include the following steps:

a) dissolving sacubitril and valsartan in a first solvent to form a first solution;

b) adding a sodium source the first solution;

c) removing the first solvent to form a reaction mass;

d) adding a second solvent to the reaction mass to form a second solution;

e) adding a third solvent to second solution; and f) isolating amorphous trisodium sacubitril valsartan.

According to this embodiment of the present invention, valsartan and sacubitril may be dissolved in a first solvent to create a first solution. Within the context of this embodiment, the solvent may act to facilitate interaction between the sacubitril, valsartan, and sodium, which may be added to the solution at a later step. The first solvent may be, for example, an alcohol solvent, an ether solvent, an ester solvent, a ketone solvent, an amide solvent, dimethyl sulfoxide, or mixtures thereof.

Examples of suitable alcohol solvents include methanol, ethanol, isopropanol, and mixtures thereof. Examples of suitable ether solvents include tetrahydrofuran, diethyl ether, 1,4-dioxane, methyl tert-butyl ether, and mixtures thereof. Examples of suitable ester solvents include methyl acetate, ethyl acetate, isopropyl acetate, tert-butyl acetate, and mixtures thereof. Examples of suitable ketone solvents include acetone, methyl ethyl ketone, methyl isobutyl ketone, or mixtures thereof. Examples of suitable amide solvents include dimethylacetamide, dimethylformamide, or a mixture thereof. In some embodiments, tetrahydrofuran and acetone were found to be particularly useful first solvents.

A sodium source may then be added to the first solution. Examples of suitable sodium sources include sodium hydroxide, sodium alkoxide, and sodium 2-ethylhexonate. In particularly useful embodiments, sodium hydroxide or sodium ethoxide is used as a sodium source.

Next, the first solvent may be removed. This may be carried out by known techniques well-known in the art, such as evaporation, distillation, or agitated thin film drying.

Next, a second solvent may be added to create a second solution. Within the context of this embodiment, the sacubitril, valsartan, sodium, and any complex that has formed is soluble in the second solvent. The second solvent may be, for example, an ester solvent, an alcohol solvent, a ketone solvent, or mixtures thereof.

Examples of suitable ester solvents include methyl acetate, ethyl acetate, isopropyl acetate, and mixtures thereof. Examples of suitable alcohol solvents include methanol, ethanol, isopropanol, and mixtures thereof. Examples of suitable ketone solvents include acetone, methyl ethyl ketone methyl isobutyl ketone, and mixtures thereof. In particularly useful embodiments, ethyl acetate is used as a second solvent.

Next, a third solvent may be added to the second solution. Within the context of this embodiment, the third solvent may facilitate isolation of the final product, for example, by precipitating out the final product as a solid. The third solvent may be more non-polar than the second solvent, for example, an alkane, a non-polar ether, or mixtures thereof. Examples of suitable alkane solvents include n-pentane, n-heptane, n-hexane, and mixtures thereof. In particularly useful embodiments, n-heptane or n-hexane are used. Examples of suitable non-polar ether solvents include methyl tert-butyl ether, diethyl ether, diisopropyl ether, and mixtures thereof.

Amorphous trisodium sacubitril valsartan may then be isolated. Isolation may be carried out by methods well known in the art, for example, by filtering and drying the obtained solid.

A further aspect of the present invention provides a process for the preparation of amorphous trisodium sacubitril valsartan, which may include the following steps:

d) dissolving trisodium sacubitril valsartan in a polar solvent to form a solution;

e) adding the solution to a non-polar solvent, and f) isolating amorphous trisodium sacubitril valsartan.

This embodiment of the present invention may be practiced by first dissolving trisodium sacubitril valsartan in a polar solvent. Within the context of this embodiment, the trisodium sacubitril valsartan may be any crystalline or solvated form. Examples of suitable polar solvents include an alcohol solvent, a ketone solvent, an ester solvent, and mixtures thereof. Examples of suitable alcohol solvents include methanol, ethanol, isopropanol, and mixtures thereof. Examples of suitable ester solvents include methyl acetate, ethyl acetate, isopropyl acetate, tert-butyl acetate, and mixtures thereof. Examples of suitable ketone solvents include acetone, methyl ethyl ketone, methyl isobutyl ketone, and mixtures thereof.

Next, the solution may be added to a non-polar solvent. The non-polar solvent may be, for example, an ether solvent or a hydrocarbon solvent. Suitable ether solvent include, for example, diethyl ether, diisopropyl ether, methyl tert-butyl ether, and mixtures thereof. Examples of hydrocarbon solvents include, for example, pentane, hexane, heptane, cyclohexane, and mixtures thereof. Within the context of this embodiment, adding the solution to the non-polar solvent may cause a precipitate to form.

Amorphous trisodium sacubitril valsartan may then be isolated. Isolation may be carried out by methods well known in the art, for example, by filtering and drying the obtained solid.

The amorphous trisodium sacubitril valsartan disclosed herein may be incorporated into oral pharmaceutical dosage forms, for example, a capsule or tablet. Dosage forms that include the amorphous sacubitril valsartan trisodium hemipentahydrate disclosed herein may be useful for reducing the risk of cardiovascular death and hospitalization for heart failure in patients with chronic heart failure and reduced ejection fraction.

The oral dosage forms containing amorphous trisodium sacubitril valsartan may further comprise one or more additional pharmaceutically acceptable excipients such as, for example, microcrystalline cellulose, hydroxypropyl cellulose, crospovidone, magnesium stearate, talc, colloidal silicon dioxide, and mixtures thereof.

Capsules or tablets containing amorphous trisodium sacubitril valsartan disclosed herein may include a coating that contains one or more excipients, artificial flavorings, artificial colorings, or mixtures thereof. For example, the coatings, may contain hypromellose, titanium dioxide, polyethylene glycol, talc, iron oxide red, iron oxide black, iron oxide yellow, or mixtures thereof. One of skill in the art will recognize a variety of excipients that would be useful for creating suitable coatings for a final dosage form of trisodium sacubitril valsartan.

Within the context of the present invention, dosage forms containing the amorphous trisodium sacubitril valsartan disclosed herein may have between about 24 mg to about 97 mg of sacubitril per dose and 26 mg to 103 mg of valsartan per dose. Particularly useful embodiments of the present invention contain 24 mg sacubitril and 26 mg valsartan, 49 mg sacubitril and 51 mg valsartan, or 97 mg sacubitril and 103 mg valsartan.

The following examples are provided to illustrate the process of the present invention. They, are however, not intended to limit the scope of the present invention in any way and several variants of these examples would be evident to person ordinarily skilled in the art.

EXAMPLES

Example 1

Preparation of Trisodium Amorphous Sacubitril Valsartan

Trisodium sacubitril valsartan (5 g) was dissolved in water (30 mL) at 25-30° C. The resulting clear solution was filtered through HYFLO at the same temperature to remove any undissolved particulate and subjected to spray drying in a laboratory Spray Dryer (Model Buchi-290) with feed rate of the solution 10 mL/min and inlet temperature at 80° C. and with 100% aspiration to yield the amorphous form of trisodium sacubitril valsartan.

Example 2

Preparation of Trisodium Amorphous Sacubitril Valsartan

Trisodium sacubitril valsartan (5 g) was dissolved in water (30 mL) at 25-30° C. The resulting clear solution was filtered through HYFLO at the same temperature to remove any undissolved particulate and subjected to lyophilization in a laboratory lyophilizer (Model Virtis Advantage Plus) to yield the amorphous form of trisodium sacubitril valsartan.

Example 3

Preparation of Amorphous Trisodium Amorphous Sacubitril Valsartan

Trisodium sacubitril valsartan (1 g) was dissolved in methanol (20 mL) at 25±5° C. The resulting clear solution was filtered through HYFLO at same temperature to remove any undissolved particulate. The obtaining clear solution was distilled completely under vacuum at 50° C. to yield the amorphous form of trisodium sacubitril valsartan.

Example 4

Preparation of Amorphous Trisodium Amorphous Sacubitril Valsartan

Trisodium sacubitril valsartan (10 g) was dissolved in tert-butyl acetate (300 mL) at 100±10° C. The resulting clear solution was filtered through HYFLO at same temperature to remove any undissolved particulate. The obtaining clear solution was reheated to 100±10° C., then cooled to 50° C. Methyl tert-butyl ether (100 mL) was added at 50° C. and the solution was cooled to 25±5° C. and maintained at that temperature for 15 hours. The obtained solid was filtered and dried at 40° C. under vacuum for 15 hours to yield the amorphous form of trisodium sacubitril valsartan.

Example 5

Preparation of Amorphous Trisodium Amorphous Sacubitril Valsartan

Sacubitril (2 g) and valsartan (2.1 g) were dissolved in tetrahydrofuran (60 mL) at 25-30° C. Aqueous sodium hydroxide solution (0.58 g NaOH in 2 mL water) was added to get a clear solution which was stirred for 30 min. The solution was then concentrated under reduced pressure at 45-50° C. to yield the amorphous form of trisodium sacubitril valsartan.

Example 6

Preparation of Amorphous Trisodium Amorphous Sacubitril Valsartan

Sacubitril (10 g) and valsartan (10.6 g) were dissolved in tetrahydrofuran (300 mL). Aqueous sodium hydroxide solution (2.92 g NaOH in 8 mL water) was added and the solution was stirred 30 min. The solution was then subjected to spray drying at 70-75° C. to yield the amorphous form of trisodium sacubitril valsartan.

Example 7

Preparation of Amorphous Trisodium Amorphous Sacubitril Valsartan

Sacubitril (10 g) and valsartan (10.6 g) were dissolved in tetrahydrofuran (300 mL). Aqueous sodium hydroxide solution was added (2.92 g NaOH in 8 mL water) and the solution was stirred for 30 min. The solution was then concentrated under vacuum to half of the total volume and tetrahydrofuran (150 mL) was again added. The solution was again concentrated to half of its volume. This solution was then subjected to agitated thin film drying at 60-65° C. under vacuum to yield the amorphous form of trisodium sacubitril valsartan.

Example 8

Preparation of Amorphous Trisodium Amorphous Sacubitril Valsartan

Sacubitril (20 g) and valsartan (21.2 g) were dissolved in tetrahydrofuran (600 mL). Aqueous sodium hydroxide solution was added (5.8 g NaOH in 16 mL water) and the solution was stirred for 30 min. The solution was then concentrated under vacuum and stripped out with tetrahydrofuran (3×100 mL) was again added concentrated completely under vacuum to yield the amorphous form of trisodium sacubitril valsartan.

Example 9

Preparation of Amorphous Trisodium Amorphous Sacubitril Valsartan

Sacubitril (5 g) and valsartan (5.1 g) were dissolved in tetrahydrofuran (60 mL) at 25-30° C. Aqueous sodium hydroxide solution (1.50 g NaOH in 4 mL water) was then added to get a clear solution and the solution was stirred for 30 min. The obtained reaction mass was concentrated under reduced pressure at 45-50° C. to get a foamy solid. Ethyl acetate (20 mL) was then added at 45-50° C. and the solution was cooled to 25-30° C. n-hexane (75 mL) was added and the solution was stirred for 2 hours at 25-30° C. The solid was filtered under nitrogen atmosphere and dried under vacuum at 35-40° C. to yield the amorphous form of trisodium sacubitril valsartan.

Example 10

Preparation of Amorphous Trisodium Amorphous Sacubitril Valsartan

Sacubitril (10 g) and valsartan (10.6 g) were dissolved in tetrahydrofuran (300 mL). Aqueous sodium hydroxide solution was added (2.9 g NaOH in 8 mL water) and the solution was stirred for 30 min. The solution was then concentrated completely under vacuum. The obtained residue was dissolved in tetrahydrofuran and again concentrated completely under vacuum. The reaction mass was cooled to ambient temperature. Ethyl acetate (30 mL) and hexane (100 mL) was added to the obtained solid, and the solution was stirred at ambient temperature for 3 hours. The obtained solid was filtered and washed with hexane to yield the amorphous form of trisodium sacubitril valsartan (20.1 g).

Example 11

Preparation of Amorphous Trisodium Amorphous Sacubitril Valsartan

Sacubitril (4.2 g) and valsartan (4.4 g) were dissolved in acetone (120 mL). Aqueous sodium hydroxide solution (1.25 g NaOH in 4 mL water) was added and the solution was stirred for 2 hours at 25-30° C. and stripped off three times with isopropyl acetate (60 mL). Isopropyl acetate (60 mL) was added to result in a clear solution. n-heptane (120 mL) was then added and to get a white solid material. The reaction mixture was stirred for 1 hour and then filtered to yield the amorphous form of trisodium sacubitril valsartan (7.7 g).

Example 12

Preparation of Amorphous Trisodium Sacubitril Valsartan

Sacubitril (10 g) and valsartan (10.6 g) were dissolved in ethanol (60 mL). Sodium hydroxide solution was added (2.92 g in 200 mL ethanol) and stirred for 30 min. The reaction mass was then concentrated under vacuum to half of the total volume. This solution was subjected to spray drying at 70-75° C. to get an amorphous form of trisodium sacubitril valsartan

Example 13

Preparation of Amorphous Trisodium Sacubitril Valsartan

Sacubitril (10 g) and valsartan (10.6 g) was dissolved in ethanol (60 mL). Sodium hydroxide solution was added (2.92 g in 200 mL ethanol) and stirred for 30 min. The reaction mass was then concentrated under vacuum to half of the total volume. This solution was subjected to agitated thin film drying at 60-65° C. under vacuum to get an amorphous form of trisodium sacubitril valsartan.

Example 14

Preparation of Amorphous Trisodium Sacubitril Valsartan

Sacubitril (10 g) and valsartan (10.6 g) was dissolved in ethanol (60 mL). Sodium hydroxide solution was added (2.92 g in 200 mL ethanol) and stirred for 30 min. The reaction mass was then concentrated until the residual volume reached to 80 mL. This solution was added drop wise to methyl tert-butyl ether (320 mL) and the solution was stirred at ambient temperature, filtered, and dried under vacuum to get an amorphous form of trisodium sacubitril valsartan.

Example 15

Preparation of Amorphous Trisodium Sacubitril Valsartan

Sacubitril (25 g) and valsartan (26.4 g) were dissolved in ethanol (125 mL). In separate flask, sodium hydroxide (7.3 g) dissolved in ethanol (500 mL), which was then added to the above clear solution of sacubitril and valsartan. The reaction mass was stirred for 30-120 minutes at 25-30° C. after which the reaction mass was concentrated under vacuum followed by stripping off three times with ethyl acetate (3×50 mL). Ethyl acetate (75 mL) was added and the solution was stirred at 40-45° C. to produce a clear solution, which was then cooled to 25-35° C. Hexanes (250 mL) were then added slowly to get precipitation of white solid material. The solution was stirred for 1 hour and filtered to get (50 g) amorphous trisodium sacubitril valsartan.

The invention claimed is:
1. A process for the preparation of amorphous trisodium sacubitril valsartan, comprising the steps of:

a. dissolving trisodium sacubitril valsartan in a solvent selected from the group consisting of an alcohol solvent, water, and mixtures thereof;
b. removing the solvent; and
c. isolating amorphous trisodium sacubitril valsartan.

2. The process according to claim 1, wherein the alcohol solvent is selected from the group consisting of methanol, ethanol, propanol, isopropanol and mixtures thereof.

3. A process for the preparation of amorphous trisodium sacubitril valsartan, comprising the steps of:
a. dissolving sacubitril valsartan trisodium hemipentahydrate in a first solvent to form a solution, wherein dissolving trisodium sacubitril valsartan is achieved at an elevated temperature from about 90° C. to about 110° C.;
b. adding a second solvent to the solution; and
c. isolating amorphous trisodium sacubitril valsartan.

4. The process according to claim 3, wherein the first solvent is a polar solvent selected from the group consisting of an alcohol solvent, an ester solvent, a ketone solvent, and mixtures thereof and the second solvent is a non-polar solvent selected from the group consisting of an ether solvent, a hydrocarbon solvent, and mixtures thereof.

5. The process according to claim 4, wherein the alcohol solvent is selected from the group consisting of methanol, ethanol, isopropanol, and mixtures thereof; the ester solvent is selected from the group consisting of methyl acetate, ethyl acetate, isopropyl acetate, tert-butyl acetate, and mixtures thereof; the ketone solvent is selected from the group consisting of acetone, methyl ethyl ketone, methyl isobutyl ketone, and mixtures thereof; the ether solvent is selected from the group consisting of diethyl ether, diisopropyl ether, methyl tert-butyl ether, and mixtures thereof; and the hydrocarbon solvent is selected from the group consisting of pentane, hexane, heptane, cyclohexane, and mixtures thereof.

6. A process for the preparation of an amorphous form of trisodium sacubitril valsartan comprising the steps of:
a. dissolving sacubitril and valsartan in a solvent to form a solution, wherein the solvent is a polar solvent selected from the group consisting of tetrahydrofuran, acetone, dimethylformamide, ethyl acetate, dimethyl sulfoxide, and mixtures thereof;
b. adding a sodium source to the solution;
c. removing the solvent; and
d. isolating amorphous trisodium sacubitril valsartan.

7. The process according to claim 6, wherein the solvent is tetrahydrofuran.

8. The process according to claim 6, wherein the sodium source is selected from the group consisting of sodium hydroxide, sodium alkoxides, and sodium ethylhexanoate.

9. A process for the preparation of amorphous trisodium sacubitril valsartan, comprising the steps of:
a. dissolving sacubitril and valsartan in a first solvent to form a solution;
b. adding a sodium source to the solution;
c. removing the first solvent;
d. adding a second solvent to form a second solution, wherein the second solvent is an organic solvent;
e. adding a third solvent to the second solution, wherein the third solvent is a non-polar solvent; and
f. isolating amorphous trisodium sacubitril valsartan.

10. The process according to claim 9, wherein the first solvent is a polar solvent selected from the group consisting of an alcohol solvent, an ether solvent, an ester solvent, a ketone solvent, an amide solvent, dimethyl sulfoxide, and mixtures thereof and the second solvent is a polar solvent selected from the group consisting of an alcohol solvent, a ketone solvent, an ester solvent, and mixtures thereof.

11. The process according to claim 10, wherein each alcohol solvent is selected from the group consisting of methanol, ethanol, isopropanol, and mixtures thereof; the ether solvent is selected from the group consisting of tetrahydrofuran, diethyl ether, 1,4-dioxane, methyl tert-butyl ether, and mixtures thereof; each ester solvent is selected from the group consisting of methyl acetate, ethyl acetate, isopropyl acetate, tert-butyl acetate, and mixtures thereof; each ketone solvent is selected from the group consisting of acetone, methyl ethyl ketone, methyl isobutyl ketone, and mixtures thereof; and the amide solvent is selected from the group consisting of dimethylacetamide, dimethylformamide, and mixtures thereof.

12. The process according to claim 9, wherein the sodium source is selected from the group consisting of sodium hydroxide, sodium alkoxides, and sodium 2-ethylhexanoate.

13. The process according to claim 9, wherein the first solvent is removed by evaporation.

14. The process according to claim 9, wherein the third solvent is a non-polar solvent selected from the group consisting of an alkane, a non-polar ether, and mixtures thereof.

15. The process according to claim 14, wherein the alkane solvent is selected from the group consisting of n-pentane, n-heptane, n-hexane, and mixtures thereof and the non-polar ether solvent is selected from the group consisting of methyl tert-butyl ether, diethyl ether, diisopropyl ether, and mixtures thereof.

* * * * *